United States Patent [19]

Jimbo et al.

[11] Patent Number: 4,719,424
[45] Date of Patent: Jan. 12, 1988

[54] MAGNETIC RESONANCE IMAGING SYSTEM

[75] Inventors: Masao Jimbo; Yukio Nanjyo, both of Ootawara, Japan

[73] Assignee: Kabushiki Kaisha Toshiba, Kawasaki, Japan

[21] Appl. No.: 897,311

[22] Filed: Aug. 18, 1986

[30] Foreign Application Priority Data

Aug. 21, 1985 [JP] Japan ................................. 60-181851
Aug. 22, 1985 [JP] Japan ................................. 60-183052

[51] Int. Cl.$^4$ ........................................... G01R 33/20
[52] U.S. Cl. ..................................... 324/309; 324/313
[58] Field of Search ............... 324/300, 307, 311, 312, 324/313, 309, 318, 322; 128/653

[56] References Cited

U.S. PATENT DOCUMENTS 4,409,550 10/1983 Fossel et al. ........................ 324/309
4,545,384 10/1985 Kawachi .............................. 324/313

Primary Examiner—Michael J. Tokar
Attorney, Agent, or Firm—Schwartz, Jeffery, Schwaab, Mack, Blumenthal & Evans

[57] ABSTRACT

An MRI system includes an MR signal acquisition section, an imaging processing section, a control signal generating section, and a control section. The MR signal acquisition section excites an MR phenomenon in a portion including a selected slice of an object to be examined, and detects MR signals generated by the MR phenomenon. The imaging processing section processes the MR signals to form an image based on MR data in the selected slice of the object. The control signal generating section generates a control signal for acquiring the MR signals in response to movement of the object. The control section controls the MR excitation operation and the MR signal acquisition operation of the MR signal acquisition section in accordance with the control signal.

11 Claims, 17 Drawing Figures

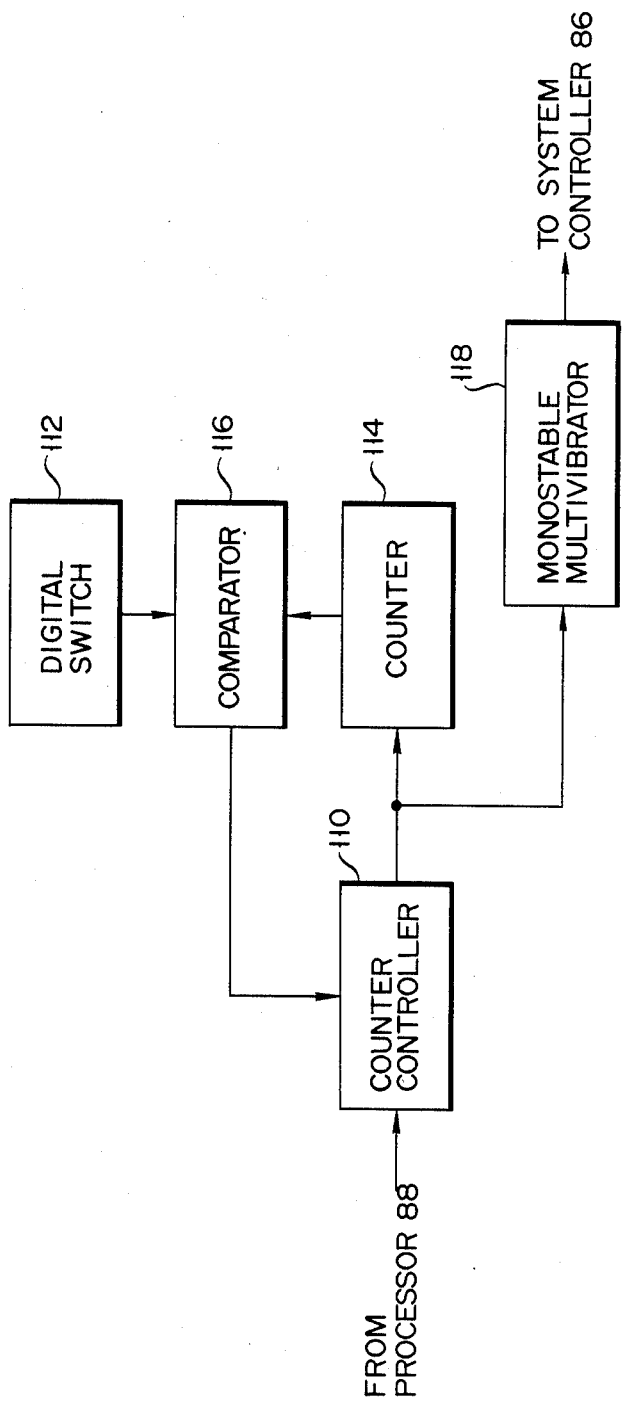

FIG.7A  REFERENCE LEVEL

MAGNETIC RESONANCE IMAGING SYSTEM

BACKGROUND OF THE INVENTION

The present invention relates to an applied technique of an MR (Magnetic Resonance) phenomenon and, more particularly, to an MRI (Magnetic Resonance Imaging) system for imaging MR data of a specific nucleus spin in a specific slice of an object to be examined.

In an MRI system, a uniform static field HO is applied to an object to be examined (i.e., a patient), and a high-frequency (radiofrequency (RF)) rotating field (electromagnetic wave) is then applied thereto to excite an MR phenomenon. An electromagnetic wave generated by the MR phenomenon is detected, to acquire MR signals. Upon excitation of the MR phenomenon and/or acquisition of the MR signals, a strength gradient (magnetic gradient) according to deviation in a specific direction is added to the static field HO, thereby causing the acquired MR signals to include positional data. Various methods for exciting the MR phenomenon and/or acquiring the MR signals are used or have been proposed. The acquired MR signals are subjected to predetermined processing to obtain an image representing a distribution of the MR data in a specific slice of a patient. In order to obtain the magnetic gradient, inclined fields Gx, Gy, and Gz along orthogonal axes X, Y, and Z of a coordinate system having the direction of static field HO given by the Z axis are selectively used. The rotating field is normally applied in the form of excitation pulses (RF pulses), the envelope of which is represented by a pulse shape. As the RF pulses, 90° pulses for changing the direction of magnetization of a nucleus spin through 90°, and/or 180° pulses for changing it through 180°, are often used.

In most methods used for exciting the MR phenomenon and/or acquiring the MR signals, the imaging sequence for obtaining an MR image can be divided into an excitation sequence for exciting the MR phenomenon and a signal acquisition sequence following the excitation sequence. A detailed imaging sequence will now be described with reference to a spin echo imaging method.

90° pulses as selective excitation pulses together with inclined field Gz along the Z axis are applied to a patient. Thereafter, inclined field Gy for encoding a phase is applied to the patient for a first predetermined period of time. After the first predetermined period of time has passed and time τ has elapsed from application of the 90° pulses, 180° pulses are applied to the patient. Thereafter, the MR signal is detected while applying inclined field Gx for a second predetermined period of time. After time τ has passed from the application of 180° pulses, a spin echo is detected as the MR signal. In this case, the period from application of the 90° pulses to that of the 180° pulses corresponds to the period of the excitation sequence. The echo detection period after application of the 180° pulses corresponds to the acquisition sequence period. After period TE, from application of the 90° pulses, has passed the spin echo is detected. The imaging sequence consisting of the excitation and acquisition sequences is repeated for cycle TR. The signals acquired during the imaging sequence are two-dimensionally Fourier-transformed for the X-Y plane to obtain image data of a given slice. During a single imaging sequence, data corresponding to one slice can be aquiered. However, in general, the data obtained after a large number of imaging sequences are integrally mixed to obtain an image for one frame, for representing the slice more clearly. Different values of inclined field Gy for phase encoding are used for every repetitive imaging sequence, and the acquired data corresponding to the respective imaging sequences are discriminated by these values of field Gy.

In the MRI system, when an MR image of a thorax or an abdomen of a patient is to be obtained, if there is any movement of a patient, such as respiratory movement or heartbeats during the MR signal acquisition sequence, the resultant MR image is blurred. In order to prevent such blurring, the imaging operation can be performed in synchronism with respiratory movement or heartbeats of a patient. In a conventional system, the imaging operation is performed simply in synchronism with respiratory movement or heartbeats. For this reason, when the imaging operation is performed in synchronism with respiratory movement having a relatively long interval, the imaging period is prolonged, and it takes a great deal of time to obtain the necessary MR image data. When the imaging operation is performed in synchronism with the heartbeats, the imaging operation cannot cope with abnormal movement such as extrasystole or arrhythmia.

SUMMARY OF THE INVENTION

It is an object of the present invention to provide an MRI system which can obtain a clear MR image without blurring of the resultant image due to the influence of movement of a patient, e.g., respiratory movement or heartbeats.

According to the present invention, there is provided an MRI system comprising: a magnetic resonance (MR) signal acquisition section for exciting a magnetic resonance (MR) phenomenon in a portion including at least a selected slice of an object to be examined and for detecting magnetic resonance (MR) signals generated by the MR phenomenon; an imaging processing section for obtaining, from the MR signals, an image based on MR data, in the selected slice of the object; a control signal generating section for generating a control signal for acquiring the MR signals in response to movement of the object; and a control section for controlling the MR phenomenon excitation operation and the MR signal acquisition operation of the MR signal acquisition section in accordance with the control signal.

According to the MRI system of the present invention, an MR signal can be acquired with an effective imaging sequence corresponding to movement of a patient, such as respiratory movement or heartbeats, and a clear MR image can be obtained while preventing the resultant image from being blurred due to the movement.

BRIEF DESCRIPTION OF THE DRAWINGS

FIG. 6 is a block diagram partially showing the arrangement shown in FIG. 5;

FIGS. 7A to 7E are timing charts for explaining the operation of the system shown in FIG. 4.

DETAILED DESCRIPTION OF THE PREFERRED EMBODIMENTS

Figure 1:
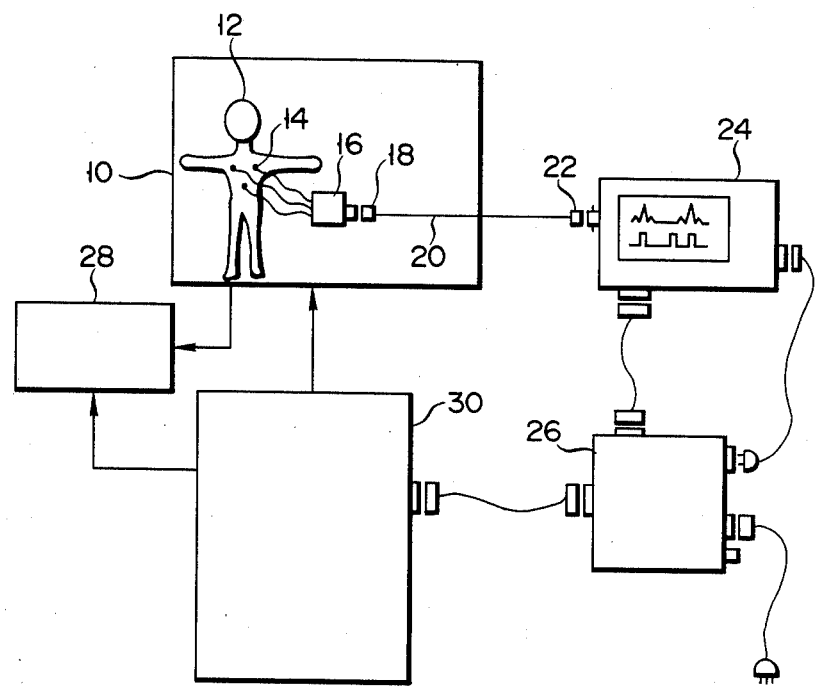
FIG. 1 is a schematic diagram of the entire MRI system according to a first embodiment of the present invention.

FIG. 1 schematically illustrates an MRI system according to a first embodiment of the present invention, in which an MR image is formed in synchronism with heartbeats.

Imaging section 10 acquires MR signals from an object to be examined (i.e., a patient). Imaging section 10 comprises a shield room, the interior of which is magnetically shielded from the exterior. In the shield room, a bed for supporting a patient, various coil devices for exciting an MR phenomenon and acquiring MR signals, and other devices necessary for acquiring the MR signals from the patient are provided. Electrodes 14 for detecting an electrocardiographic signal are mounted on patient 12 lying in imaging section 10. Electrodes 14 are connected to amplifier 16 for amplifying the detected electrocardiographic signal. An output from amplifier 16 is converted to a photo signal by electric/photo converter 18 consisting of light emitting elements. Patient 12, electrodes 14, amplifier 16, and converter 18 are arranged in the shield room. The electrocardiographic signal converted to the photo signal by converter 18 is guided outside the shield room through optical transmission path 20 consisting of, for example, optical fibers, and is converted to an electrical signal by photo/electric converter 22. The electrical signal (electrocardiographic signal) is supplied from converter 22 to electrocardiograph unit 24. Unit 24 retrieves the electrocardiographic signal, generates a QRS sync signal sychronous with a QRS wave of the electrocardiographic signal, and displays a QRS sync signal waveform and an aquisition timing signal waveform (to be described later). Sync control unit 26 generates an excitation instruction signal and an acquisition stop instruction signal in response to the QRS sync signal generated from unit 24.

Imaging processor 28 processes the MR signals acquired by imaging section 10, to obtain an MR image of a selected slice, i.e., an image based on spin density distribution data or relaxation time (vertical relaxation or horizontal relaxation) distribution data or a combination of these data.

System controller 30 controls imaging section 10 and imaging processor 28, and performs a series of sequence control operations for imaging an MR image. System controller 30 uses the excitation instruction signal and the acquisition stop instruction signal as interruption inputs, and controls the MR excitation sequence and the acquisition sequence of the MR signals in response to these signals.

Note that electrodes 14, amplifier 16, electric/photo converter 18, and optical transmission path 20 are formed of non-magnetic material, so as not to disturb the field generated for MR excitation and data acquisition.

Figure 2:
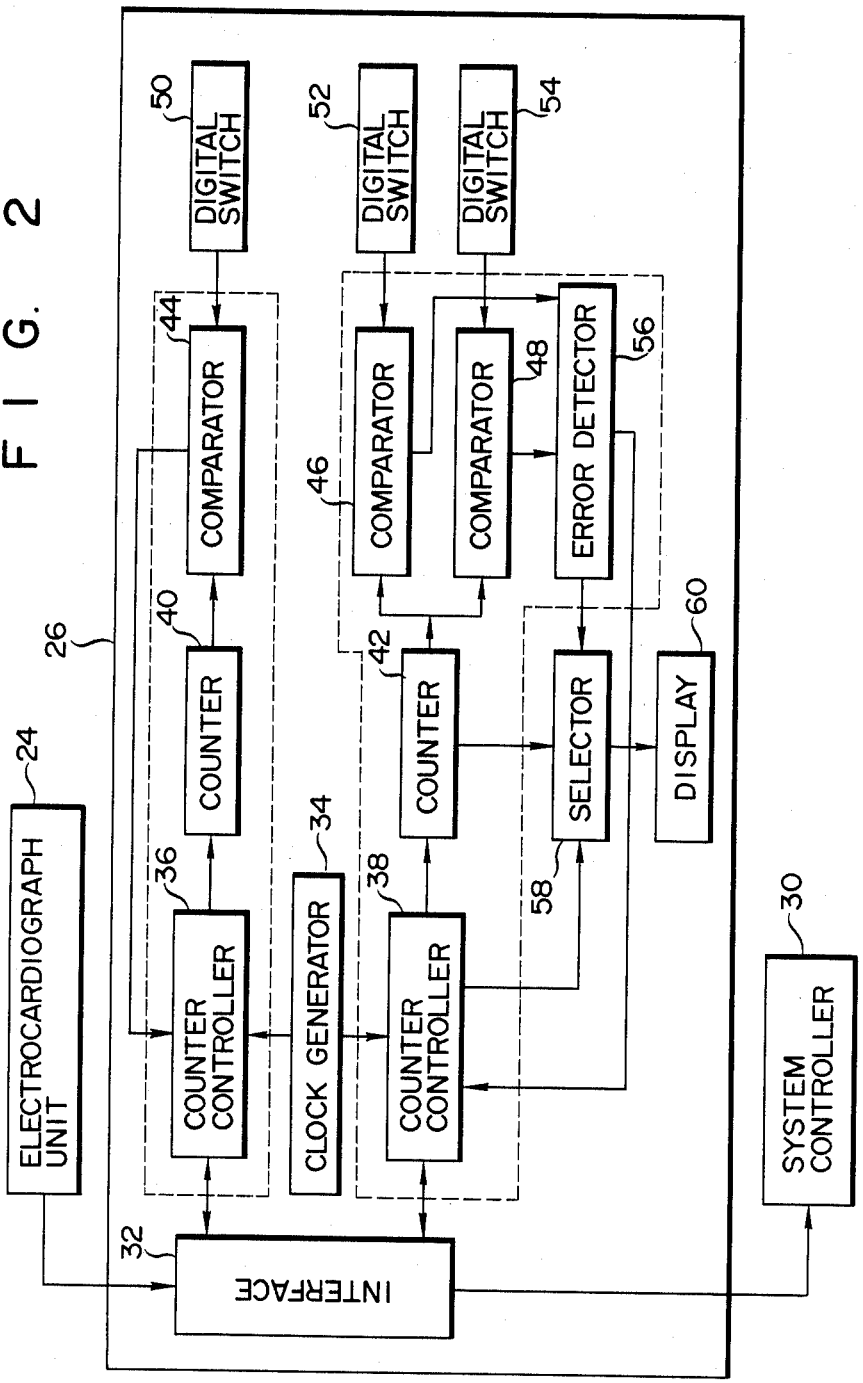
FIG. 2 is a detailed block diagram of the main part of the system shown in FIG. 1.

The detailed arrangement of sync control unit 26 will now be described with reference to FIG. 2.

Sync control unit 26 comprises interface 32, clock generator 34, first and second counter controllers 36 and 38, first and second counters 40 and 42, first, second, and third comparators 44, 46, and 48, first, second, and third digital switches 50, 52, and 54, error detector 56, selector 58, and display 60.

Interface 32 performs, for example, necessary level adjustment, and exchanges signals with an external circuit. Interface 32 supplies the excitation instruction signal and the acquisition stop instruction signal to system controller 30 upon reception of the QRS sync signal from electrocardiograph unit 24. Clock generator 34 generates clock pulses having a 1-msec period. When numerical values are set to digital switches 50, 52, and 54, they produce data representing these values. Digital switches 50, 52, and 54 are used for setting a cardiac phase for the imaging operation, the upper limit, and the lower limit of a normal R wave period, respectively.

A section consisting of counter controller 36, counter 40, comparator 44, and digital switch 50 produces the excitation instruction signal for initiating MR excitation in a given slice of the patient in a desired cardiac phase, based on the QRS sync signal retrieved through interface 32. Counter 40 counts the clock pulses generated by generator 34 and transferred through counter controller 36. The count of counter 40 is compared with numerical data from switch 50 by comparator 44, and the comparison result is supplied from comparator 44 to counter controller 36. Counter controller 36 controls the operation of counter 40 and the transferring of clock pulses supplied from generator 34 to counter 40, in response to the QRS sync signal from interface 32 and the comparison result signal from comparator 44. In addition, controller 36 supplies the excitation instruction signal to interface 32.

A section consisting of counter controller 38, counter 42, comparators 46 and 48, digital switches 52 and 54, and error detector 56 measures a repetitive period of the R wave of the electrocardiographic signal with reference to the QRS sync signal fetched through interface 32. When the measured result falls outside a predetermined range, the acquisition stop instruction signal for stopping acquisition of the MR signals is generated. Counter 42 counts the clock pulses generated from generator 34 and transferred through counter controller 38. The count of counter 42 is compared with numerical data supplied from digital switches 52 and 54, by comparators 46 and 48, respectively. The comparison results are supplied from comparators 46 and 48 to error detector 56. Error detector 56 determines an error based on the comparison results from comparators 46 and 48 when the R wave falls outside the predetermined range, and supplies the error detection signal to counter controller 38. Counter controller 38 controls the operation of counter 42 and the transferring of clock pulses from generator 34 to counter 42, and supplies the acquisition stop instruction signal to interface 32.

Selector 58 selects one of the outputs from counter controller 38, counter 42, and error detector 56, and the selected output is displayed on display 60.

The detailed operation of this system will now be described with reference to FIGS. 3A to 3E.

Figures 3A, 3B, 3C, 3D, 3E:
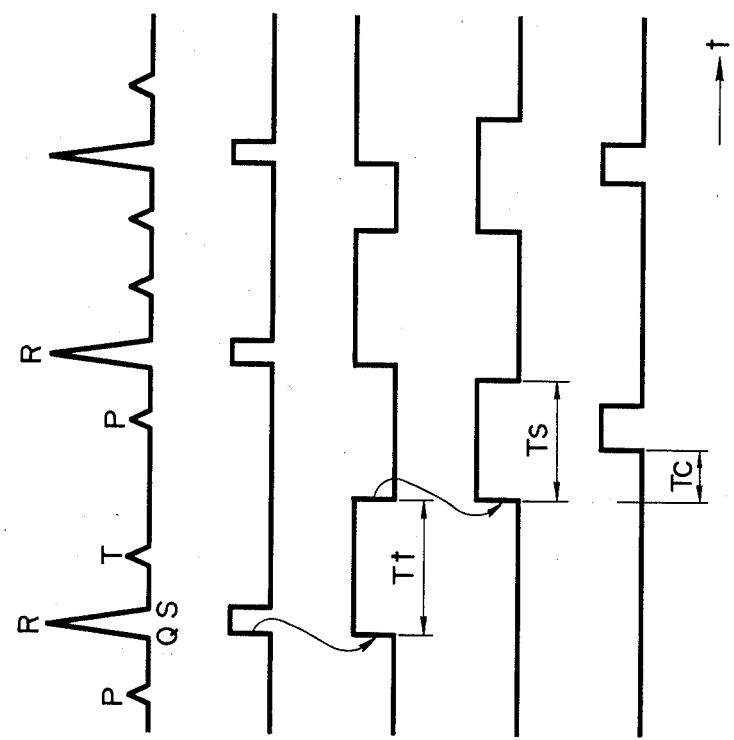
FIGS. 3A to 3E are timing charts for explaining the operation of the system shown in FIG. 1.

FIG. 3A shows the electrocardiographic signal; FIG. 3B, the QRS sync signal synchronous with the QRS wave of the electrocardiograph waveform; FIG. 3C, the excitation instruction signal output from sync control unit 26 (in this case, excitation is initiated in response to the falling edge of the waveform); FIG. 3D, an excitation sequence signal generated by system controller 30; and FIG. 3E, the acquisition timing signal.

The electrocardiographic signal is detected and amplified by amplifier 16 through electrodes 14 mounted on patient 12. The electrocardiographic signal is converted to a photo signal by electric/photo converter 18, and is transferred to photo/electric converter 22 through optical transmission path 20. The photo signal supplied to converter 22 is converted to an electrical signal, and is then input to electrocardiograph unit 24. Unit 24 produces the QRS sync signal synchronous with the QRS wave of the electrocardiographic signal, based on the input electrical signal, i.e., the electrocardiographic signal. The QRS sync signal is displayed on the display of unit 24, together with the input electrocardiographic signal.

The QRS sync signal from unit 24 is supplied to sync control unit 26, and is then input to counter controllers 36 and 38 through interface 32.

Counter controller 36 is triggered in response to the rising edge of the QRS sync signal, and sets the logic state of the excitation instruction signal output through interface 32 from L (low) level to H (high) level (excitation is not initiated). At the same time, controller 36 causes clock generator 34 to begin to supply clock pulses to counter 40. Counter 40 counts the clock pulses, and the count thereof is continuously supplied from counter 40 to comparator 44. Comparator 44 compares the count with the set value by means of digital switch 50. From the comparison result, if the count of counter 40 exceeds the set value of switch 50, the output state of comparator 44 is inverted. In response to this inversion, an output from counter controller 36 to interface 32, i.e., the excitation instruction signal, goes from H level to L level. At the same time, transferring of clock pulses from counter controller 36 to counter 40 is stopped, and counter 40 is cleared. The above operation is repeated for every QRS sync signal.

The excitation instruction signal is supplied from interface 32 to system controller 30. System controller 30 generates the excitation sequence signal and the acquisition timing signal for the MR image in response to the excitation instruction signal. More specifically, in response to the falling edge of the excitation instruction signal, the excitation sequence signal is generated from system controller 30, and excitation of the MR phenomenon for a predetermined slice of the patient 12 is started. In this manner, the MR phenomenon is excited in a predetermined slice of patient 12. After predetermined time Tc has passed, from the beginning of the excitation sequence, the acquisition timing signal is generated from system controller 30, and the MR signals for the predetermined slice of patient 12 are acquired during the H-level interval of the timing signal. The acquired MR signals are supplied to imaging processor 28. Imaging processor 28 processes the input MR signals to form image data based on the MR data. The acquisition timing signal is also supplied to electrocardiograph unit 24 and is displayed on its display. The acquisition timing signal is displayed to be superimposed on, for example, the QRS sync signal. An operator monitors this display to ascertain the acquisition timing of the MR signals. As a matter of course, when the set value of digital switch 50 is changed, time Tt, from the rising edge of the QRS sync signal to the falling edge of the excitation instruction signal, can be changed. Therefore, the operator can set the acquisition timing in a desired cardiac phase of the electrocardiographic signal while observing the waveforms displayed on unit 24.

Even if the MR signal acquisition is performed in synchronism with a cardiac phase, when heartbeats are irregular upon generation of extrasystole or arrhythmia, the shifting of the cardiac phase occurs, and the resultant MR image is often blurred.

In contrast to this, in the system of this embodiment, the repeating cycle of the R wave of the electrocardiographic signal, i.e., the upper and lower limits of the allowable range of the R wave interval, can be set by second and third digital switches 52 and 54. If the pulse interval, i.e., the R wave interval, of the QRS sync signal obtained from electrocardiograph unit 24 falls outside the allowable range, the MR signal acquisition is stopped and the MR image can be prevented from being blurred. The acquisition stop instruction signal for stopping the MR signal acquisition is generated from sync control unit 26.

The QRS sync signal generated from electrocardiograph unit 24 is supplied to counter controller 38. Counter controller 38 transfers the clock pulses generated by clock generator 34 to second counter 42 during an interval from the first to the second rising edge of the QRS sync signal (the repeating cycle of the R wave). Counter 42 counts the input clock pulses, and the count thereof is supplied to second and third comparators 46 and 48. When the counting operation of counter 42 ends (i.e., when the next counting operation starts), its count is output and latched, and it is then cleared. In comparator 46, the count of counter 42 is compared with the set value of digital switch 52 (the upper limit of the allowable R wave interval). In comparator 48, the count of counter 42 is compared with the set value of digital switch 54 (the lower limit of the allowable R wave interval). If the output state of comparator 46 or 48 is changed from a normal state (in which the R wave interval falls within the range between its upper and lower limits), this means that the R wave interval is longer than the set value of digital switch 52 or is shorter than that set by digital switch 54. When error detector 56 detects from the outputs of comparators 46 and 48 that the R wave interval falls outside the allowable range, it supplies the acquisition stop instruction signal to counter controller 38. Counter controller 38 transfers the acquisition stop instruction signal to system controller 30 through interface 32. Upon reception of the acquisition stop instruction signal, system controller 30 stops the MR signal acquisition regardless of the presence/absence of the excitation instruction signal. When MR signal acquisition is stopped, the immediately preceding QRS sync signal is prevented from contributing to MR image formation. For example, when MR signal acquisition is stopped, if the excitation instruction signal and the excitation sequence signal associated with the immediately preceding QRS sync signal are not generated, output of the next excitation instruction signal and the next excitation sequence signal is suppressed. If excitation has already been initiated, acquisition of further MR signals is inhibited. In addition, when MR signal acquisition has already been started, the MR signal data already acquired in response to the immediately preceding QRS sync signal is made invalid. Of course, MR signal acquisition based on the immediately preceding QRS sync signal can be interrupted by other methods, to ensure it doesn't contribute to MR image formation. When a new QRS sync signal is supplied, measurement of a cardiac phase and R wave interval is restarted.

If it is taken into consideration that a normal R wave interval in a human body is about 800 msec, the upper and lower limits of the R wave interval are set at about 880 and 720 msec, respectively, by digital switches 52 and 54.

In the system of the present invention, MR signal acquisition can be performed in a desired cardiac phase based on the electrocardiographic signal. In addition, when the R wave interval falls outside the predetermined allowable range, MR signal acquisition is stopped. Therefore, when an MR image in a slice of the heart, blood system, or a portion therearound of a patient is to be obtained, blurring of the MR image caused by movement of the heart or blood system, or extrasystole or arrhythmia of the heart, and the like, can be eliminated or removed, thus providing a clear MR image. Since electrodes 14, amplifier 16, and converter 18 are formed of non-magnetic material, a clear MR image can be advantageously obtained without disturbing a field applied to the patient for MR signal acquisition.

Note that a means for transferring the electrocardiographic signal can comprise a radio transmitter for transmitting the electrocardiographic signal using an electric wave, and a receiver for receiving the transmitted electric wave to derive the electrocardiographic signal therefrom. In this case, the transmitter is preferably formed of a non-magnetic material so as not to disturb a field.

An MRI system according to a second embodiment of the present invention will now be described. In this embodiment, MR signal acquisition is performed in synchronism with the respiratory movement of the patient.

Figure 4:
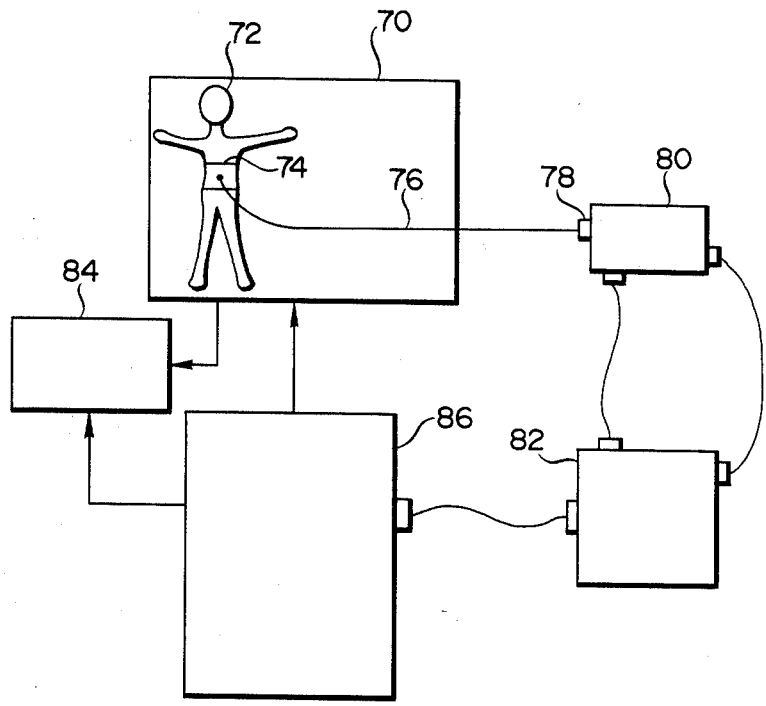
FIG. 4 is a schematic diagram of the entire MRI system according to a second embodiment of the present invention.

FIG. 4 schematically shows the arrangement of the second embodiment of the present invention. In this case, the MR signal acquisition method synchronous with an electrocardiograph can also be used in addition to the method of this embodiment. However, FIG. 4 illustrates the arrangement for obtaining the MR signals in synchronism with respiratory movement.

Imaging section 70 for acquiring MR signals from a patient comprises a shield room, the interior of which is magnetically shielded from the exterior. In the shield room, a bed for supporting a patient, various coil devices for exciting an MR phenomenon and acquiring MR signals, and other devices necessary for acquiring the MR signal from the patient, are provided. Air bag 74 for detecting respiratory movement of patient 72 is mounted on patient 72 lying in imaging section 70. Air bag 74 is made of a flexible material and comprises a bag-like member in which air is appropriately sealed and has a fabric belt for attaching. Air bag 74 is mounted to be in tight contact with the thorax or the abdomen of patient 72 by means of the fabric belt, and the internal pressure of the bag-like member changes in accordance with the respiratory movement of patient 72. The bag-like member of air bag 74 is coupled to one end of pressure transmission tube 76. The other end of tube 76 extends outside the shield room of imaging section 70, and is coupled to multiplexer 80 through pressure sensor 78. Pressure sensor 78 detects the internal pressure of air bag 74 transmitted by tube 76, converts it into an electrical signal, and supplies it to multiplexer 80. In this embodiment, multiplexer 80 incorporates an A/D (analog-to-digital) converter. Multiplexer 80 converts the input electrical signal to a digital signal and fetches it to remove a noise component therefrom. Thereafter, multiplexer 80 supplies the resultant signal to sync control unit 82. Multiplexer 80 fetches another analog signal and converts it into a digital signal, in addition to fetching a respiration signal from pressure sensor 78, and multiplexes it with the respiration signal to supply the multiplexed signal to sync control unit 82. In this case, although not shown, an electrocardiographic signal of patient 72 is input to multiplexer 80, and an excitation instruction signal synchronous with a cardiac phase obtained by the same arrangement as in the first embodiment is supplied to sync control unit 82. Sync control unit 82 generates an excitation instruction signal in response to the respiration signal output from pressure sensor 78.

Imaging processor 84 processes MR signals acquired by imaging section 70, and forms an MR image in a selected slice of patient 72, i.e., an image based on spin density distribution data or relaxation time (vertical relaxation or horizontal relaxation) distribution data or a combination of these data.

System controller 86 controls imaging section 70 and imaging processor 84, and performs a series of sequence control operations for imaging an MR image. System controller 86 uses the excitation instruction signal supplied from control unit 82 as an interruption input, and controls the MR excitation/acquisition sequence in response thereto.

Needless to say, air bag 74, tube 76, and the like arranged in the shield room of imaging section 70 are formed of a non-magnetic material, so as not to disturb a field generated for MR excitation and data acquisition.

Figure 5:
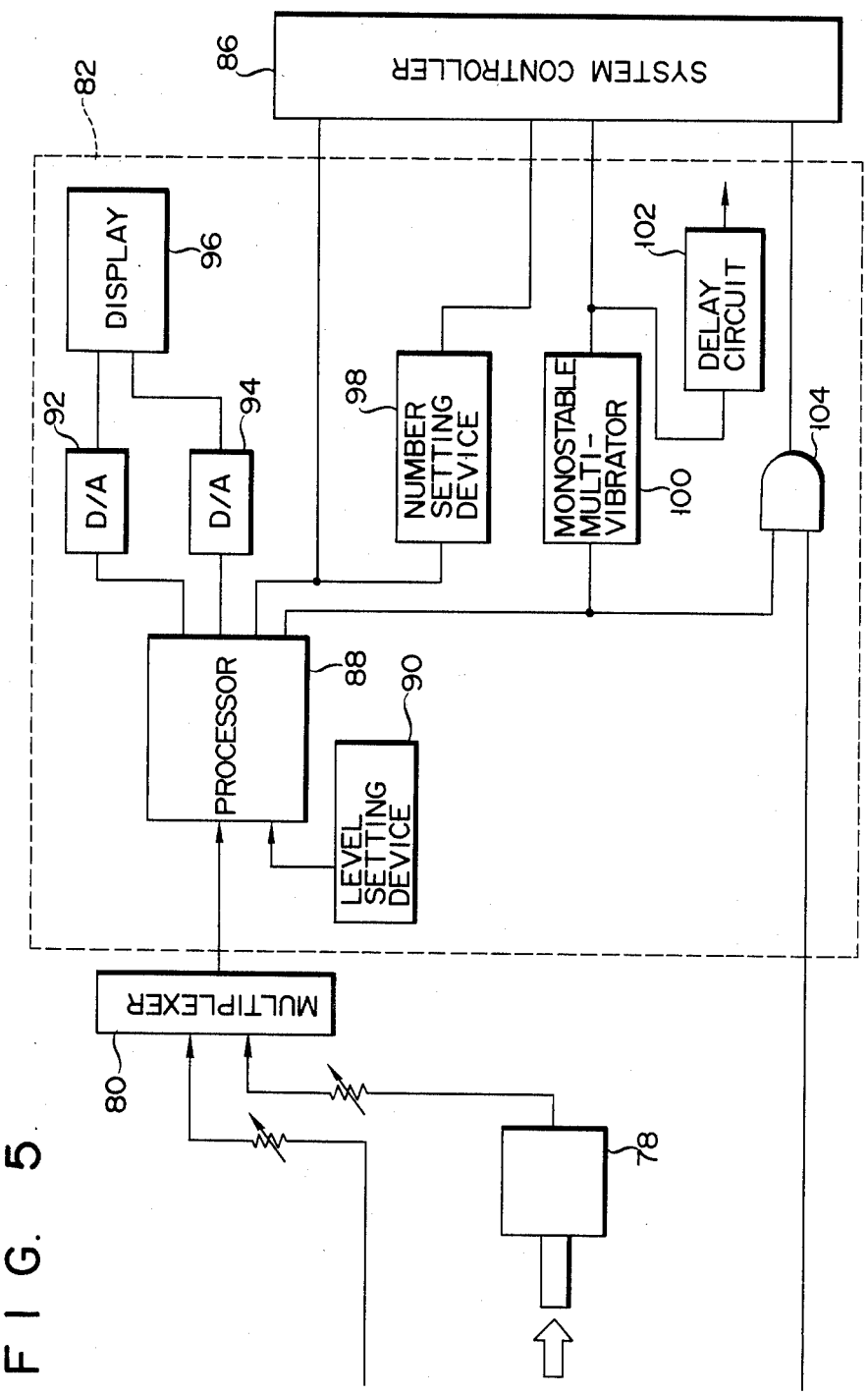
FIG. 5 is a detailed block diagram of the main part of the system shown in FIG. 4.

The detailed arrangement of sync control unit 82 will now be described with reference to FIG. 5.

Sync control unit 82 comprises processor 88, level setter 90, first and second D/A (digital-to-analog) converters 92 and 94, display 96, number setter 98, monostable multivibrator 100, delay circuit 102, and AND gate 104.

Processor 88 receives outputs from multiplexer 80 and level setter 90. Level setter 90 outputs a preset comparison reference level for the respiration signal. The reference level of setter 90 is arbitrarily set by, for example, a manual operation. In this system, MR signal acquisition is performed only when the respiration signal falls within a predetermined level range. This level range is set by setter 90. More specifically, MR signal acquisition is performed during an interval in which the respiration signal is below the reference level set by setter 90. Note that MR signal acquisition can be performed during an interval in which the respiration signal exceeds the reference level. Alternatively, MR signal acquisition can be performed during an interval in which the respiration signal falls outside the reference level range set by level setter 90. In this case, level setter 90 is arranged to set upper and lower limit levels. Processor 88 demultiplexes the multiplexed signal from multiplexer 80 into the electrocardiographic signal and the respiration signal, and outputs them. At the same time, processor 88 compares the demultiplexed respiration signal with the reference level from level setter 90, and generates a comparison result signal based on the comparison result. The electrocardiographic signal and the respiration signal from processor 88 are converted to analog signals respectively by D/A converters 92 and 94, and are displayed on display 96. The comparison result signal from processor 88 is supplied to system controller 86, number setter 98, monostable multivibrator 100, and AND gate 104.

Number setter 98 comprises counter controller 110, digital switch 112, counter 114, comparator 116, and monostable multivibrator 118, as shown in FIG. 6. Counter controller 110 transfers the comparison result signal to counter 114 which counts it. The count of counter 114 is compared with a set value of digital switch 112 by comparator 116. When the count has reached the set value, a control signal is supplied to counter controller 110, and transferring of the comparison result signal to counter 114 is interrupted. The comparison result signal output from counter controller 110 is also supplied to monostable multivibrator 118, is waveshaped thereby, and is then supplied to system controller 86. In other words, the signal supplied from monostable multivibrator 118 to system controller 86 is a pulse string having a repeating pulse number preset by digital switch 112.

Monostable multivibrator 100 waveshapes the comparison result signal from processor 88, and supplies the shaped signal to delay circuit 102. Delay circuit 102 delays the output of monostable multivibrator 100 by a predetermined period of time and then outputs it. The output of multivibrator 100 is supplied as a freeze instruction signal to an ultrasonic diagnosis apparatus (not shown). The output from monostable multivibrator 100 is delayed so as to allow an ultrasonic image of the ultrasonic diagnosis apparatus to be frozen in synchronism with MR signal acquisition. AND gate 104 logically ANDs the comparison result signal and the excitation instruction signal synchronous with the cardiac phase, and outputs a signal in which the respiration signal falls within the allowable range and which is synchronized with the electrocardiographic signal.

The detailed operation of this system will now be described with reference to FIGS. 7A to 7E.

Figures 7B, 7C, 7D, 7E:
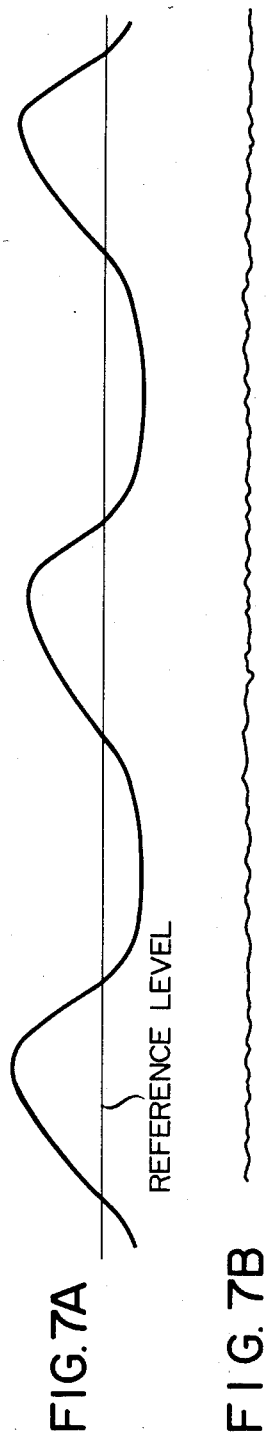

FIG. 7A shows the respiration signal; FIG. 7B, the electrocardiographic signal; FIG. 7C, the comparison result signal; and FIGS. 7D and 7E, two different excitation/acquisition sequences by means of system controller 86.

An operator operates level setter 90 to set a reference level while observing the respiration signal (FIG. 7A) and the electrocardiographic signal (FIG. 7B) provided on display 96. After the reference level is set, the comparison result signal (FIG. 7C) of the reference level and the respiration signal is generated from processor 88. Normally, system controller 86 is operated in response to the comparison result signal, and MR excitation and MR signal acquisition are performed during the H-level period of the comparison result signal for, for example, 500-msec repetitive cycle TR. At this time, when the ultrasonic diagnosis apparatus is frozen in response to the output from delay circuit 102, an ultrasonic diagnosis slice image can be freeze-displayed in synchronism with the MR image acquisition timing, and can be subjected to diagnosis in comparison to the MR image. If a data acquisition number is set by digital switch 112 of number setter 98, MR signal acquisition can be performed a preset number of times.

If another number setter is provided in system controller 86, the excitation/acquisition sequences, i.e., number of the excitation/acquisition within the pulse width period of the comparison result signal can be set.

In addition, a method for acquiring the MR data includes a method in which excitation/acquisition sequences are repeated from the beginning of the H-level interval of the comparison result signal, as shown in FIG. 7D, and a method in which only MR phenomenon excitation is performed at the beginning of each acquisition sequence and, thereafter, excitation/acquisition sequences are repeated to acquire MR signals having uniform characteristics, taking MR signal precision into consideration, as shown in FIG. 7E. These methods can be selected by system controller 86.

Figure 8:
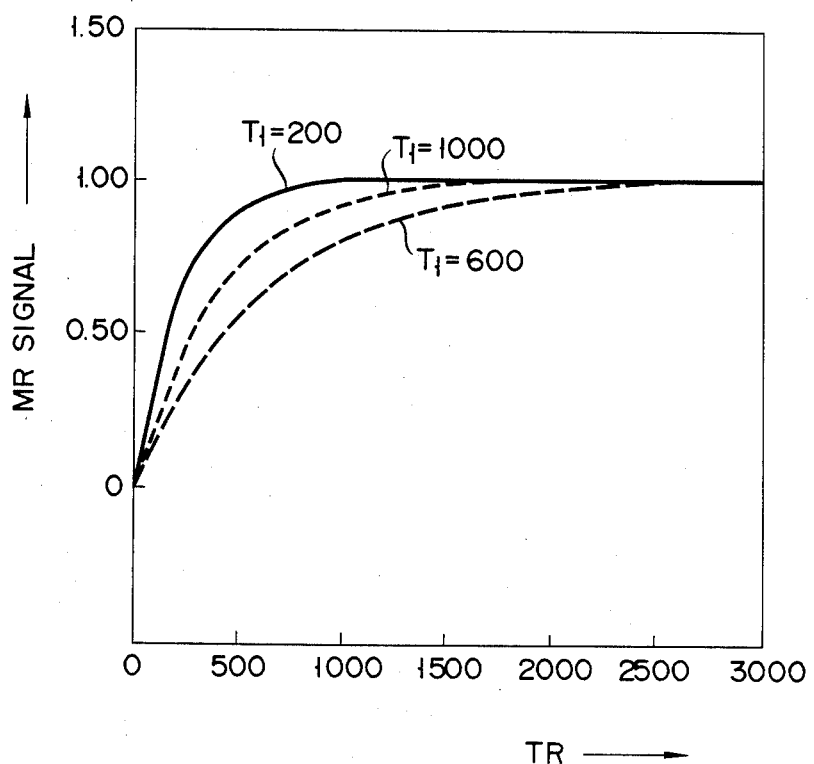
FIGS. 8 and 9 are graphs for explaining the second embodiment shown in FIG. 4.
Figure 9:
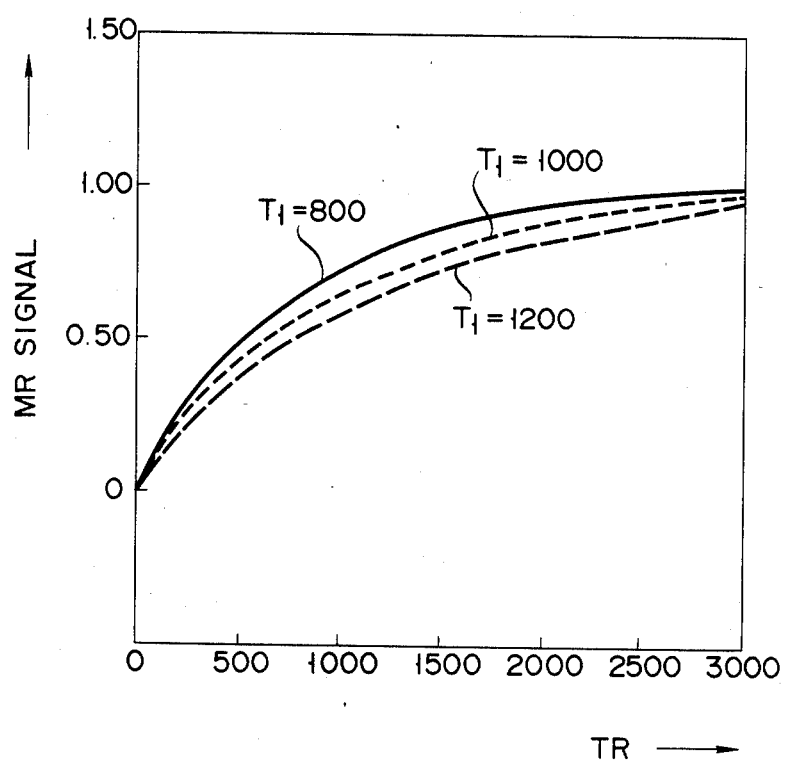

The above methods will now be compared with reference to FIGS. 8 and 9.

MR signal I is given by the following relation, and when repeating time TR is changed, MR signal I obtained from tissue having the same vertical relaxation time T1 changes:

$$I \propto \{1 - \exp(-TR/T1)\}$$

In FIGS. 8 and 9, the level of MR signal I from tissue having the same time T1 changes upon change of time TR. For example, referring to FIG. 9, a signal intensity ratio for T1=1000 changes to about 1.6 times (1.56=0.7/0.45) when TR changes from 500 to 900. Therefore, the value of T1 of normal tissue depends on field intensity HO (normally, 200 to 1000 ms), and as can be seen from these graphs, it is important to adjust time TR.

Note that the present invention is not limited to the embodiments described above with reference to the drawings, and various changes and modifications may be made within the spirit and scope of the invention.

For example, a means for detecting movement of an object to be examined can comprise a thermistor formed of a non-magnetic material near the nostrils of a patient, to detect a change in temperature due to respiratory movement. The detection signal can be used as a respiration signal. Alternatively, a tube in which the non-magnetic conductive material (e.g., Hg, ZnCl, and the like) is sealed is wound around the trunk (including the thorax) of the patient, and movement of the object can be detected from a change in impedance of the non-magnetic conductive material.

What is claimed is:

1. A magnetic resonance imaging system for producing an image of an object corresponding to magnetic resonance (MR) signals from a portion of the object of interest, said MR signals collected in synchronization with a periodic displacement of the object comprising:
    magnetic resonance signal acquisition means for exciting a magnetic resonance phenomenon in said portion of interest of the object including at least a selected slice of said object to be examined, and for detecting magnetic resonance (MR) signals generated by the MR phenomenon;
    imaging processing means for forming an image based on said detected magnetic resonance signals induced from said selected slice;
    monitoring means for monitoring said displacement of the object, said monitoring means generating a predetermined detectable signal caused by said displacement, and producing a control signal representative of said periodic displacement of the object; and
    control means for controlling an excitation operation and collection of said induced MR signals in accordance with said control signal, said control means including means for inhibiting at least one of (1) collection of said MR signals and (2) reconstruction of the image of the object when the periodic displacement of the object occurs irregularly.

2. A system according to claim 1, wherein said monitoring means comprises movement detecting means, formed of non-magnetic material, for obtaining a movement signal having an amplitude corresponding to a deviation caused by the movement of the object, and amplitude discriminating means for supplying the control signal to said control means when the movement signal satisfies a predetermined level condition.

3. A system according to claim 2, wherein said movement detecting means comprises a detecting member which is formed of a hollow flexible material, mounted to be in tight contact with the object, and in which a gas is sealed, and a pressure sensor for converting the internal pressure of said detecting member into an electrical signal.

4. A system according to claim 2, wherein said movement detecting means includes means for detecting respiratory movement of the object.

5. A system according to claim 2, wherein said control means further comprises number setting means for setting the number of times of a series of MR excitation-/acquisition sequences occur within a predetermined period of time.

6. A system according to claim 2, wherein said control means comprises means which only performs an excitation operation and does not perform a signal acquisition operation during a first series of MR excitation/acquisition sequences within a predetermined period of time.

7. A system according to claim 2, wherein said amplitude discriminating means includes means for selectively setting the level condition.

8. A system according to claim 1, wherein said monitoring means comprises electrocardiographic signal detecting means, formed of a non-magnetic material, for detecting an electrocardiographic signal of the object, and phase control means for supplying the control signal to said control means in a desired phase, in response to the electrocardiographic signal.

9. A system according to claim 8, wherein said inhibiting means inhibits the output of the control signal when a repeating cycle of a predetermined waveform portion of the electrocardiographic signal falls outside a preset range.

10. A system according to claim 8, wherein said monitoring means further comprises signal transferring means for transferring the electrocardiographic signal from said electrocardiographic signal detecting means to said phase control means.

11. A system according to claim 8, wherein said signal transferring means comprises electric/photo converting means for converting the electrocardiographic signal into a photo signal, an optical transmission path for transferring the photo signal therethrough, and photo/electric converting means for converting the photo signal supplied from said electric/photo converting means into an electrical signal.

* * * * *